(12) United States Patent
Petersen

(10) Patent No.: US 10,177,604 B2
(45) Date of Patent: Jan. 8, 2019

(54) RESONANT POWER TRANSFER SYSTEMS HAVING EFFICIENCY OPTIMIZATION BASED ON RECEIVER IMPEDANCE

(71) Applicant: TC1 LLC, St. Paul, MN (US)

(72) Inventor: Ethan Falk Petersen, Oakland, CA (US)

(73) Assignee: TC1 LLC, St. Paul, MN (US)

(*) Notice: Subject to any disclaimer, the term of this patent is extended or adjusted under 35 U.S.C. 154(b) by 66 days.

(21) Appl. No.: 15/286,930

(22) Filed: Oct. 6, 2016

(65) Prior Publication Data
US 2017/0104369 A1 Apr. 13, 2017

Related U.S. Application Data

(60) Provisional application No. 62/238,586, filed on Oct. 7, 2015.

(51) Int. Cl.
*H02J 50/12* (2016.01)
*A61M 1/12* (2006.01)
(Continued)

(52) U.S. Cl.
CPC ............ *H02J 50/12* (2016.02); *A61M 1/127* (2013.01); *H02J 7/025* (2013.01); *A61M 2205/8243* (2013.01); *H02J 50/80* (2016.02)

(58) Field of Classification Search
CPC . H02J 5/005; H02J 7/025; H02J 17/00; B60L 11/182
See application file for complete search history.

(56) References Cited

U.S. PATENT DOCUMENTS 4,041,955 A 8/1977 Kelly et al.
4,352,960 A 10/1982 Dormer et al.
(Continued)

FOREIGN PATENT DOCUMENTS

DE 202012000166 U1 6/2013
DE 102012201073 A1 7/2013
(Continued)

OTHER PUBLICATIONS

Q. Chen, S.C. Wong, C.K. Tse, X. Ruan, "Analysis, design, and control of a transcutaneous power regulator for artificial hearts", Jan. 20, 2009, IEEE, IEEE Transactions on biomedical circuits and systems, vol. 3, Issue 1, pp. 23-31.*

(Continued)

*Primary Examiner* — Rexford Barnie
*Assistant Examiner* — David Shiao
(74) *Attorney, Agent, or Firm* — Armstrong Teasdale LLP

(57) ABSTRACT

The present disclosure provides systems and methods for controlling wireless power transfer systems. A wireless power transfer system includes a transmitter driven by a power source and a transmit controller, wherein the transmitter is configured to control delivery of wireless power, and a receiver inductively coupled to the transmitter, the receiver configured to receive the wireless power from the transmitter and deliver the received wireless power to a load. The receiver includes receiver electronics configured to determine a Thevenin equivalent impedance of the wireless power transfer system, determine a Thevenin equivalent source voltage of the wireless power transfer system, and control, based on the determined Thevenin equivalent impedance and the determined Thevenin equivalent source voltage, an ideal source voltage of the receiver to vary the amount of the wireless power transferred from the transmitter to the receiver.

18 Claims, 9 Drawing Sheets

(51) Int. Cl.
*H02J 7/02* (2016.01)
*H02J 50/80* (2016.01)

(56) References Cited

U.S. PATENT DOCUMENTS

| | | |
|---|---|---|
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 4,945,305 A | 7/1990 | Blood |
| 5,070,223 A | 12/1991 | Colasante |
| 5,346,458 A | 9/1994 | Affeld |
| 5,350,413 A | 9/1994 | Miller et al. |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1 | 11/2001 | Sato et al. |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,400,991 B1 | 6/2002 | Kung |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 5/2005 | Amundson et al. |
| 6,949,065 B2 | 9/2005 | Sporer et al. |
| 6,960,968 B2 | 11/2005 | Odenaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | Lafranchise et al. |
| 7,565,187 B1 | 7/2009 | Dynok et al. |
| 7,571,007 B2 | 8/2009 | Erickson et al. |
| 7,574,173 B2 | 8/2009 | Terranova et al. |
| 7,587,241 B2 | 9/2009 | Parramon et al. |
| 7,599,743 B2 | 10/2009 | Hassler, Jr. et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,741,734 B2 | 6/2010 | Joannopoulos et al. |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson et al. |
| 7,962,222 B2 | 6/2011 | He et al. |
| RE42,682 E | 9/2011 | Barreras et al. |
| 8,076,801 B2 | 12/2011 | Karalis et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbunaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Smith et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,694,117 B2 | 4/2014 | Aghassian et al. |
| 8,810,071 B2 | 8/2014 | Sauerlaender et al. |
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,106,083 B2 | 8/2015 | Partovi |
| 9,192,704 B2 | 11/2015 | Yomtov et al. |
| 9,302,093 B2 | 4/2016 | Mashiach |
| 9,515,494 B2 | 12/2016 | Kurs et al. |
| 9,515,495 B2 | 12/2016 | Kurs et al. |
| 9,560,787 B2 | 1/2017 | Kallmyer et al. |
| 2002/0038138 A1 | 3/2002 | Zarinetchi et al. |
| 2002/0087204 A1 | 7/2002 | Kung et al. |
| 2002/0093456 A1 | 7/2002 | Sawamura et al. |
| 2003/0171792 A1 | 9/2003 | Zarinetchi et al. |
| 2004/0138725 A1 | 7/2004 | Forsell |
| 2004/0256146 A1 | 12/2004 | Frericks |
| 2005/0006083 A1 | 1/2005 | Chen et al. |
| 2005/0090883 A1 | 4/2005 | Westlund et al. |
| 2005/0288743 A1 | 12/2005 | Ahn et al. |
| 2006/0199997 A1 | 9/2006 | Hassler et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0191706 A1 | 8/2007 | Calderon et al. |
| 2008/0009198 A1 | 1/2008 | Marino |
| 2008/0027293 A1 | 1/2008 | Vodermayer et al. |

(56) References Cited

U.S. PATENT DOCUMENTS

| | | |
|---|---|---|
| 2008/0054638 A1 | 3/2008 | Greene et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0211320 A1 | 9/2008 | Cook et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0174264 A1 | 7/2009 | Onishi et al. |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066176 A1* | 3/2010 | Azancot ............ H02J 5/005 307/104 |
| 2010/0066305 A1 | 3/2010 | Takahashi et al. |
| 2010/0069992 A1 | 3/2010 | Aghassian et al. |
| 2010/0102639 A1 | 4/2010 | Joannopoulos et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | Digiore et al. |
| 2011/0025132 A1 | 2/2011 | Sato |
| 2011/0043050 A1 | 2/2011 | Yabe et al. |
| 2011/0046699 A1 | 2/2011 | Mazanec |
| 2011/0057607 A1 | 3/2011 | Carobolante |
| 2011/0101790 A1 | 5/2011 | Budgett |
| 2011/0109263 A1 | 5/2011 | Sakoda et al. |
| 2011/0115431 A1 | 5/2011 | Dunworth et al. |
| 2011/0127848 A1 | 6/2011 | Ryu et al. |
| 2011/0148215 A1 | 6/2011 | Marzetta et al. |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1 | 5/2012 | Carobolante |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153739 A1 | 6/2012 | Cooper et al. |
| 2012/0153954 A1 | 6/2012 | Ota et al. |
| 2012/0155136 A1* | 6/2012 | Von Novak ............ H02J 5/005 363/126 |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0235364 A1 | 9/2012 | Wang et al. |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0119773 A1 | 5/2013 | Davis |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1 | 7/2013 | Callaway et al. |
| 2013/0197607 A1 | 8/2013 | Wilder et al. |
| 2013/0214731 A1 | 8/2013 | Dinsmoor |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0042821 A1* | 2/2014 | Boys ............ H02J 5/005 307/104 |
| 2014/0092649 A1* | 4/2014 | Hsu ............ H02J 5/005 363/34 |
| 2014/0152252 A1 | 6/2014 | Wood |
| 2014/0163644 A1 | 6/2014 | Scott et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |
| 2015/0123654 A1 | 5/2015 | Gagnon et al. |
| 2015/0202970 A1* | 7/2015 | Huang ............ B60L 11/1829 320/108 |
| 2015/0207330 A1 | 7/2015 | Petersen |
| 2015/0207331 A1 | 7/2015 | Petersen |
| 2015/0222127 A1 | 8/2015 | Hansen |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0249345 A1* | 9/2015 | Kashiwagi ............ H02J 5/005 307/104 |
| 2015/0290373 A1* | 10/2015 | Rudser ............ A61M 1/1086 623/3.27 |
| 2016/0135684 A1 | 5/2016 | Kappel et al. |
| 2016/0218432 A1 | 7/2016 | Pope et al. |
| 2016/0250484 A1 | 9/2016 | Nguyen et al. |

(56) References Cited

U.S. PATENT DOCUMENTS

| | | |
|---|---|---|
| 2016/0254703 A1 | 9/2016 | Hansen |
| 2016/0254704 A1 | 9/2016 | Hansen et al. |

FOREIGN PATENT DOCUMENTS

| | | |
|---|---|---|
| EP | 0589608 A2 | 9/1993 |
| EP | 1513241 A1 | 3/2005 |
| EP | 2267864 A2 | 6/2010 |
| GB | 2477034 A | 7/2011 |
| JP | H03109063 A | 5/1991 |
| JP | 11-506646 | 6/1999 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120007296 | 1/2012 |
| KR | 1020120077448 | 7/2012 |
| WO | 0001442 A2 | 1/2000 |
| WO | 74747 A1 | 12/2000 |
| WO | 137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |

OTHER PUBLICATIONS

A. Costanzo, M. Dionigi, D. Masotti, M. Mongiardo, G. Monti, L. Tarricone, R. Sorrentino, Electromagnetic energy harvesting and wireless power transmission: a unified approach, Oct. 7, 2014, IEEE, Proceedings of the IEEE, vol. 102, Issue 11, p. 1692-1711.*

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.

Chargepoint, Inc.; -chargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filing date and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Meru, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Meru, Francesco, et al.," the Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

* cited by examiner

RESONANT POWER TRANSFER SYSTEMS HAVING EFFICIENCY OPTIMIZATION BASED ON RECEIVER IMPEDANCE

CROSS REFERENCE TO RELATED APPLICATIONS

This application claims priority to U.S. Provisional Patent Application No. 62/238,586, filed Oct. 7, 2015, which is hereby incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The field relates generally to resonant wireless power transfer systems, and more specifically to communication systems and methods for implantable resonant wireless power transfer systems.

BACKGROUND

Many types of devices require transmitting energy between locations. Recent advances have accelerated the pace of innovation for wireless energy transmission (WET) without the use of cords. An example of a system using wireless energy technology is a powered, implantable medical device.

Many implantable medical devices require electrical systems to power the implant. Typically, this is achieved using percutaneous wiring to connect a power source to the implant. More recently, there has been interest in development of Transcutaneous Energy Transfer (TET) systems, e.g., through an oscillating magnetic field, for powering implantable medical devices.

A TET system usually includes a number of components or systems. A conventional TET system is implemented with a transmitting coil and a receiving coil for transmitting energy across the skin layer. The system typically includes a controller for driving the transmitting coil and/or controlling the implanted electronics.

Typically, implantable medical devices, such as implanted sensors, require very little power to operate. With such low power levels (on the order of milliwatts), power transfer levels and efficiency can be lower. With higher power devices (e.g., on the order of watts and up to 15 W or more), efficient transfer of wireless power is extremely important. Additionally, positions within the body are limited that can accommodate larger implanted devices, some of which are deep below the skin surface. These implant locations require additional attention to position and orientation of both the transmit and receive coils, as well as techniques to improve and maximize transfer efficiency.

Previous TET systems for implantable medical devices required the implanted receiver coil to be positioned just under the skin, and typically include a mechanical feature to align the receive and transmit coils and keep them together. By implanting these devices directly under the skin, the size and power requirements of these implanted devices is limited if they are to be powered by a TET system. TET systems can be designed for operation even while power is not being received by the receiver coil. In a typical configuration, solid-state electronics and a battery can power the implanted medical device when external power is interrupted or not available.

For higher power devices, efficiency and heat losses become very important. Heat loss in an implanted device is limited by the acceptable temperature rise of the surrounding tissue. Typically a 2° C. temperature rise in tissue is the acceptable limit before risking thermal damage to the surrounding tissue. This is a relatively small temperature rise, meaning the acceptable heat loss in an implant is also small. As a result, the power efficiency of a TET system is very important.

BRIEF DESCRIPTION

In one embodiment, the present disclosure is directed to a wireless power transfer system. The wireless power transfer system includes a transmitter driven by a power source and a transmit controller, wherein the transmitter is configured to control delivery of wireless power, and a receiver inductively coupled to the transmitter, the receiver configured to receive the wireless power from the transmitter and deliver the received wireless power to a load. The receiver includes receiver electronics configured to determine a Thevenin equivalent impedance of the wireless power transfer system, determine a Thevenin equivalent source voltage of the wireless power transfer system, and control, based on the determined Thevenin equivalent impedance and the determined Thevenin equivalent source voltage, an ideal source voltage of the receiver to vary the amount of the wireless power transferred from the transmitter to the receiver.

In another embodiment, the present disclosure is directed to a receiver for use in a wireless power transfer system. The receiver is configured to receive wireless power from a transmitter driven by a power source and a transmit controller, and configured to deliver the received wireless power to a load. The receiver includes a receiving coil, and receiver electronics coupled to the receiving coil. The receiver electronics are configured to determine a Thevenin equivalent impedance of the wireless power transfer system, determine a Thevenin equivalent source voltage of the wireless power transfer system, and control, based on the determined Thevenin equivalent impedance and the determined Thevenin equivalent source voltage, an ideal source voltage of the receiver to vary the amount of the wireless power transferred from the transmitter to the receiver.

In yet another embodiment, the present disclosure is directed to a method for controlling a wireless power transfer system. The wireless power transfer system includes a receiver inductively coupled to a transmitter, the receiver configured to receive wireless power from the transmitter and deliver the received wireless power to a load. The method includes determining, using receiver electronics at the receiver, a Thevenin equivalent impedance of the wireless power transfer system, determining, using the receiver electronics, a Thevenin equivalent source voltage of the wireless power transfer system, and controlling, using the receiver electronics, based on the determined Thevenin equivalent impedance and the determined Thevenin equivalent source voltage, an ideal source voltage of the receiver to vary the amount of the wireless power transferred from the transmitter to the receiver.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
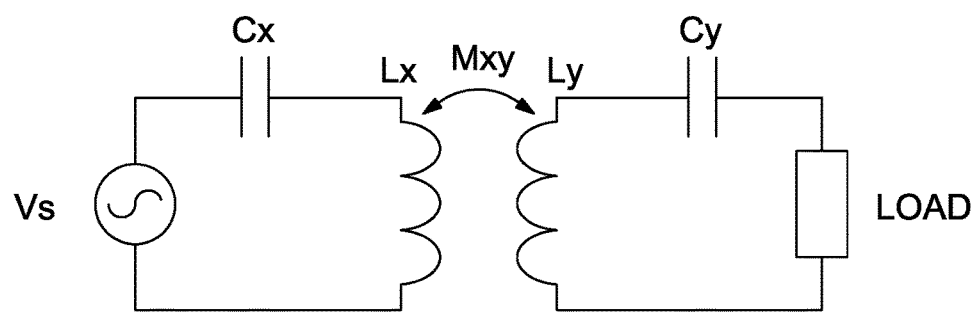
FIG. 1 illustrates a basic wireless power transfer system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the disclosure are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/0027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter. In some cases, "loosely coupled" or "loose coupling" refers a highly resonant system and/or a system using strongly-coupled magnetic resonators.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. Examples of closely coupled system with resonant coils are described in International Pub. Nos. WO2001/037926; WO2012/087807; WO2012/087811; WO2012/087816; WO2012/087819; WO2010/030378; and WO2012/056365, U.S. Pub. No. 2003/0171792, and U.S. Pat. No. 5,350,413 (now abandoned), incorporated herein for all purposes by reference.

For given coil sizes and separations, coupling a given amount of power requires generating the same magnetic field strength for either inductive or resonant systems. This requires the same number of ampere-turns in the coils. In inductive systems, all the ampere-turns pass through the MOSFETs and generate power losses in their on-state resistance. In resonant systems, only the exciter ampere-turns pass through the MOSFETs, while the resonator ampere-turns do not. As a consequence, resonant systems will always have lower losses and higher efficiencies than inductive systems of the same dimensions and power through-put.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$M_{xy} = k\sqrt{L_x \cdot L_y}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency of the system, f, is 250 kHz. Then, for each cycle the load removes a certain amount of energy from the resonance:

$$e_L = \frac{P_L}{f} = 60 \ \mu J \quad \text{Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self inductance of the receiver coil was found to be 60 uH. From the energy and the inductance, the voltage and current in the resonator could be calculated.

$$e_y = \frac{1}{2} L i^2$$

$$i_y = \sqrt{\frac{2e_y}{L}} = 3.74 \ \text{A peak}$$

$$v_y = \omega L_y i_y = 352 \ \text{V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that $k$ is 0.05:

$$e_x = \frac{420 \ \mu J}{0.05} = 8.4 \ mJ$$

For the same circuit the self inductance of the transmitter coil was 146 uH as mentioned above. This results in:

$$i_x = \sqrt{\frac{2e_x}{L}} = 10.7 \ \text{A peak}$$

$$v_x = \omega L_x i_x = 2460 \ \text{V peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
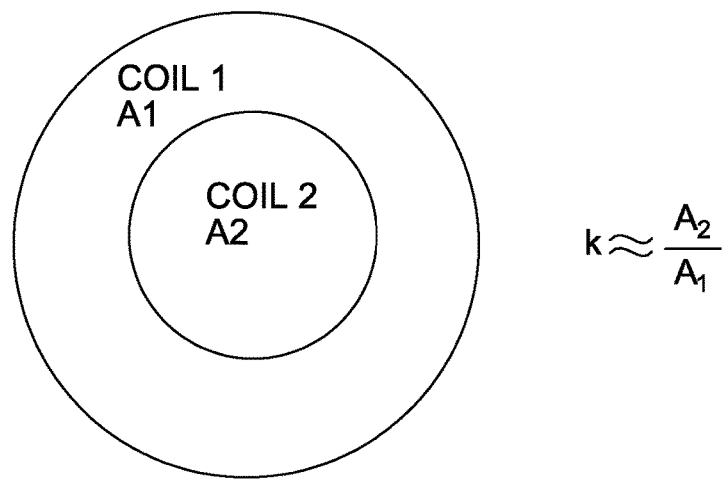
FIG. 2 illustrates the flux generated by a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
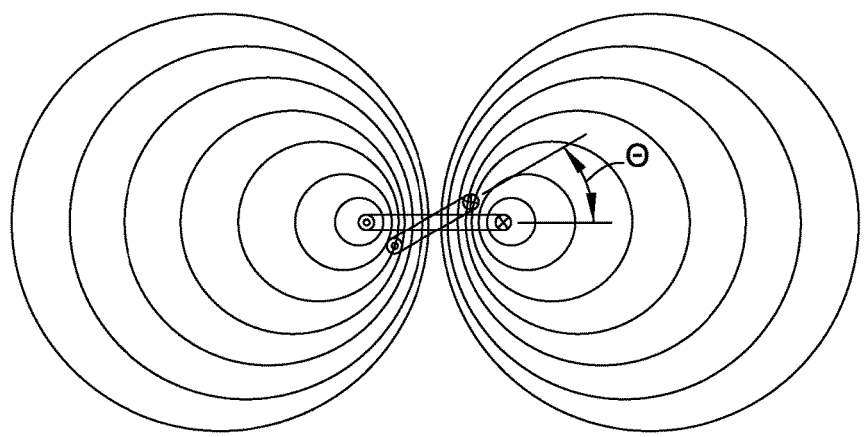
FIGS. 3A-3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta ($\theta$) is 90 degrees, the flux will not be received by the receiver and the coupling coefficient will be zero.

Figure 3B:
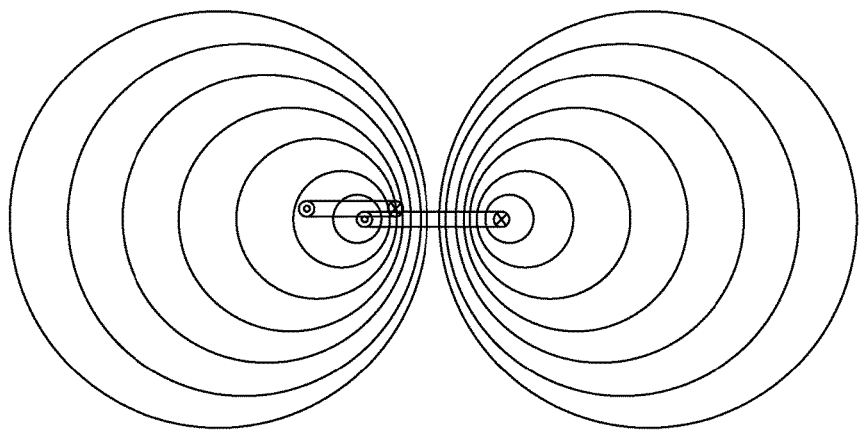

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

Figure 4:
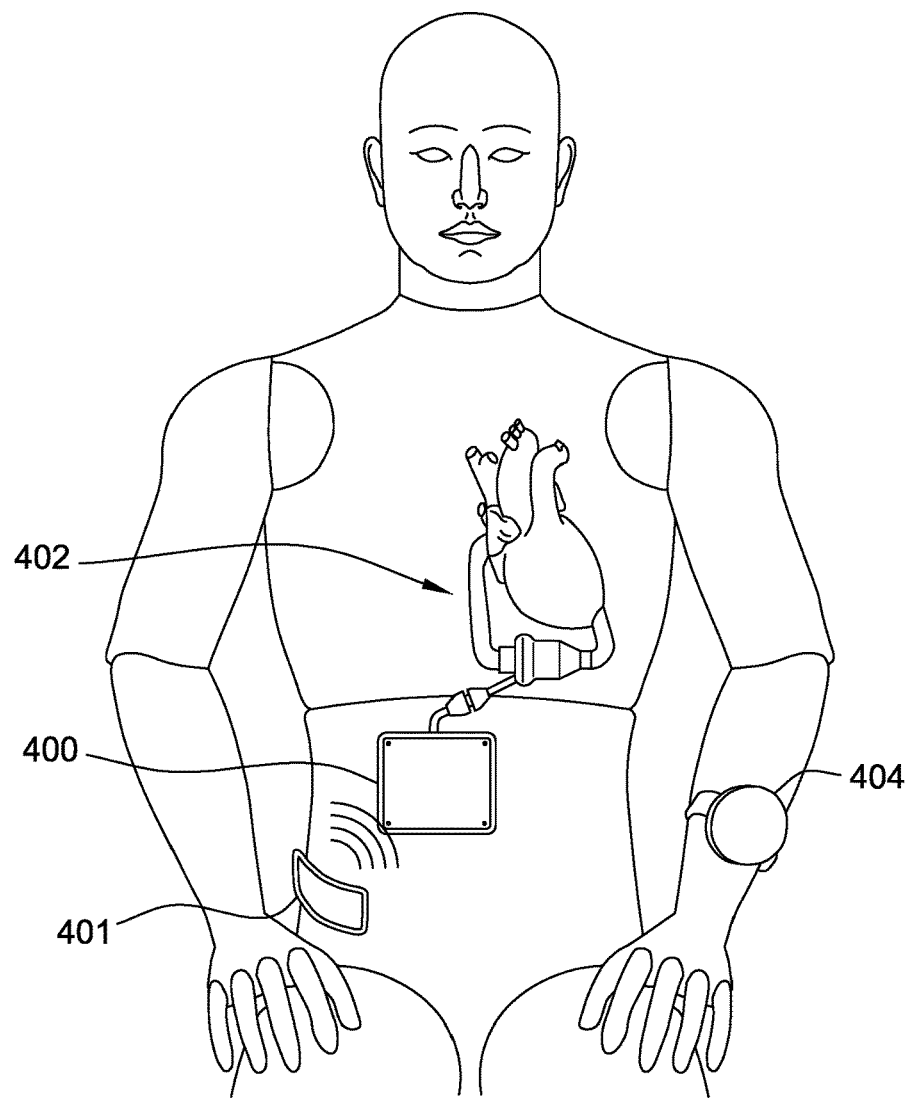
FIG. 4 illustrates a wireless power transfer system comprising an implantable TETS receiver unit implanted in an abdomen of a human patient.

FIG. 4 illustrates a wireless power transfer system comprising an implantable TETS receiver unit 400 implanted in an abdomen of a human patient. The receiver unit 400 can be coupled to a device load 402, such as an implantable medical device, e.g., an implantable LVAD or heart pump. The exemplary receiver unit 400 can include a receiver resonator coil and electronics configured to receive wireless energy from an external transmitter 401, which can include a power supply such as a pulse generator connected to a transmitter resonator coil. In one embodiment, the electronics and coils are implanted separately and connected by an implanted cable. In some embodiments, external controller 404 can be configured to communicate with the TETS receiver unit 400 and can be worn by the patient, such as on the patient's wrist. In other embodiments, the external controller can be an electronic computing device such as a personal computer, a tablet, smartphone, or laptop computer.

In some embodiments, the receiver unit 400 further includes communications electronics configured to send and receive communications data to and from other electronic devices inside and outside of the body. In one embodiment, the receiver unit further includes an internal rechargeable power source. In various embodiments, the receiver unit 400 of the TET system is configured as a single implanted device including the receive coil, antenna, power source, and associated circuitry. The receiver unit is configured so the implantable medical device can be plugged directly into the unit. The single housing configuration makes implantation easier and faster. Additionally, since there are less implants, and consequently less tunneling in the body and percutaneous defect sites, adverse event risks like bleeding and infection are reduced. One of skill will appreciate from the description herein that various internal components of the system can be bundled together or implanted separately. For example, the internal rechargeable power source can be implanted separately from the receiver unit and connected by a power cable. The antenna assembly, power source, and receive coil can all be configured in separate hermetically sealed housings. International Pub. No. WO2007/053881A1, U.S. Pub. No. 2014/0005466, and U.S. Pat. No. 8,562,508, the entire contents of which are incorporated herein for all purposes by reference, disclose several exemplary configurations.

TET systems of the present disclosure provide solutions for optimizing efficiency to maximize battery life and to minimize heat in both the implanted receiver and the external transmitter. The most efficient operating condition is where the current in the resonant system is as small as possible. However, if the current is too small, the TET system will not be able to transfer enough power. If the TET system tries to pull more power out of the resonators than can be supported, the resonant system collapses which results in no power transfer.

According to the present disclosure, the receiver unit can be configured to monitor the impedance of the transmit and receive resonators and calculate the amount of power than can be transferred through the TET system. The receiver unit can use this calculated amount of power to limit how much power the receiver unit pulls out of the resonant system and avoid collapse of the system. If the receiver unit requires more power than it is pulling from the resonant system, the receiver unit can communicate the need for more power to the transmitter unit (e.g., by transmitting a control message from the receiver to the transmitter), which can then drive the resonators with more current to transfer additional power. This allows the TET system to run at the minimum amount of current required to transfer the desired amount of power, which minimizes losses in the system.

The receiver can communicate with the transmitter using any suitable communications techniques. For example, TETs power signals between the transmitter and receiver may be modulated to communicate information between the transmitter and receiver. Alternatively, a separate radio may be used to send messages from the receiver to the transmitter. Further, optical or acoustic communication methods may be used as well. U.S. Pub. No. 2015/0222139, which is incorporated by reference herein in its entirety, discussion communications between a receiver and a transmitter in a wireless energy transfer system.

Figure 5:
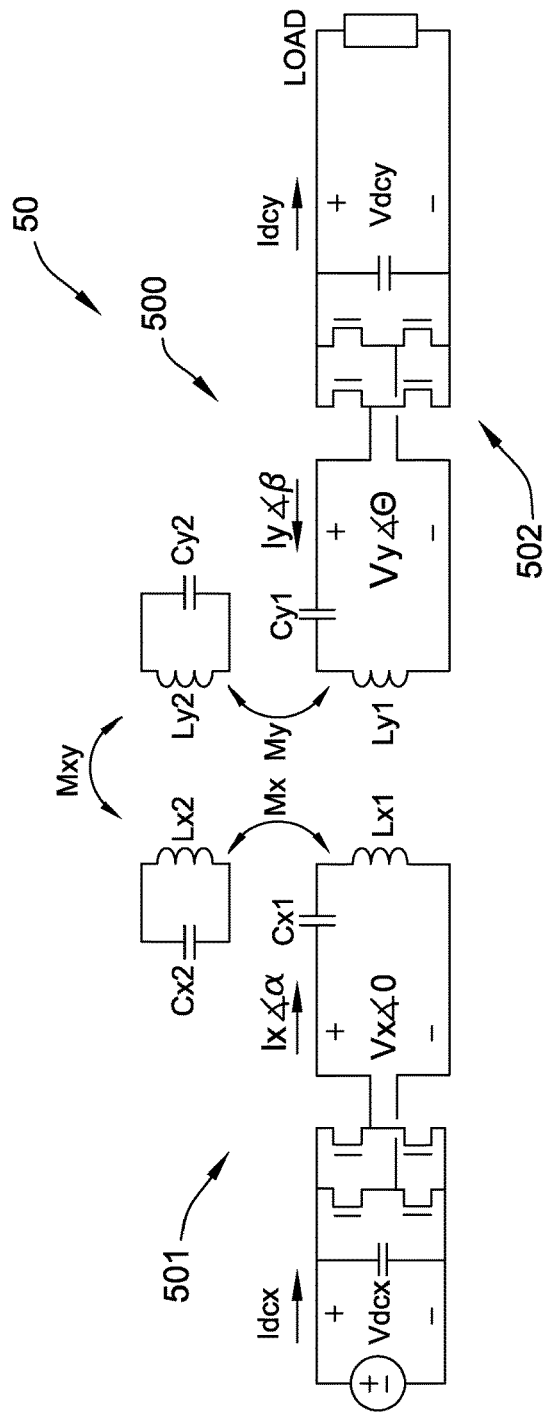
FIG. 5 illustrates one embodiment of a TET system 5, including a receiver and a transmitter.

FIG. 5 illustrates one embodiment of a TET system 50, including a receiver 500 and a transmitter 501. The circuit shown in FIG. 5 can further modeled as a two port network, shown in FIG. 6. The transmitter power electronics are modeled as an ideal voltage source, Vx. The receiver power electronics are also modeled as an ideal voltage source, Vy. The currents and voltages are described using a phasor notation.

Figure 6:
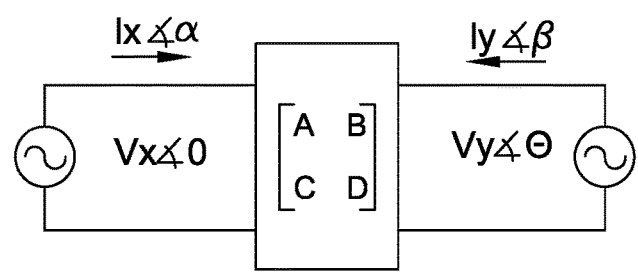
FIG. 6 illustrates the circuit of FIG. 5 modeled as a two port network.
Figure 7:
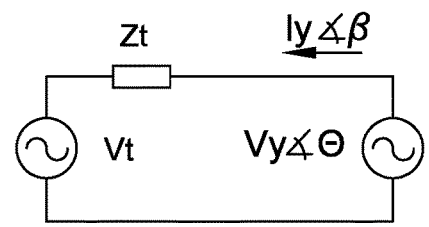
FIG. 7 shows the two port network of FIG. 6 modeled as a Thevenin equivalent circuit.

From the point of view of the receiver, the two port network of FIG. 6 can be represented by the Thevenin equivalent circuit. The resonant system appears to be a voltage source and an impedance, as shown in FIG. 7. The impedance Zt is a function of the resonant system's inductance and capacitance, so it changes as the mutual coupling between the transmitter and the receiver changes. The relative position of the transmitter and receiver changes the impedance Zt. The voltage source Vt changes both magnitude and phase as a function of the mutual coupling, and the transmitter voltage Vx.

Figure 8:
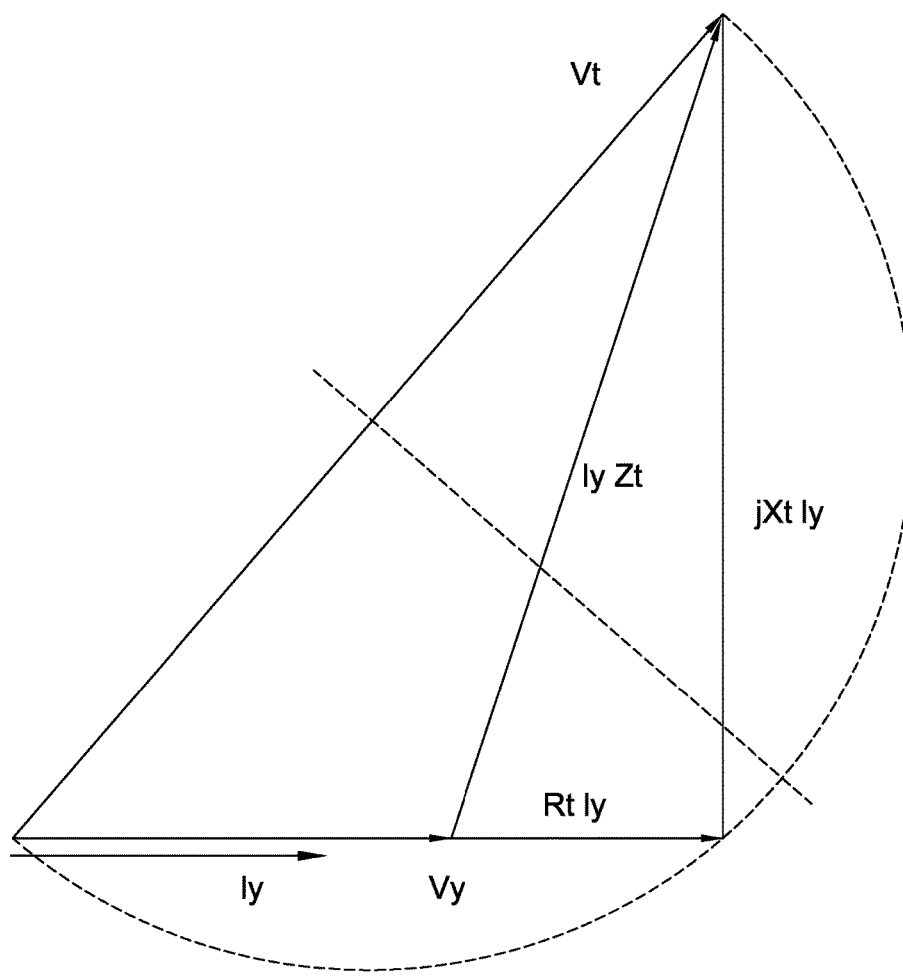
FIG. 8 shows operation of the circuit of FIG. 5 as illustrated by a phasor diagram.

The receiver electronics are able to control the voltage source, Vy, to get a specific voltage magnitude and phase. The operation of the circuit is illustrated by the phasor diagram in FIG. 8. This diagram shows the voltage source Vy is controlled to be in phase with the current Iy. The TET system is configured to transfer the maximum amount of power when the magnitude of Vy is equal to the magnitude of IyZt. To control the power through the resonators, the circuit can be controlled in a couple ways, including:

Method 1: For many systems the magnitude of Vt and Zt are large. There is a limit to the magnitude of Vy. In the system shown in FIG. 5, the limit is the DC bus voltage of the receiver. If Vt is large relative to Vy, the power through the system can be controlled by adjusting the magnitude of Vy. Increasing Vy increases the amount of power through the system.

Method 2: In another embodiment, the way to control the amount of power only works if the magnitude of Vt is smaller than the largest possible magnitude of Vy. If Vy is equal to Vt then no power is transferred through the system. As Vy is reduced then the amount of power absorbed by the receiver increases.

To avoid having the receiver try to pull more power than the system can handle, it is possible to limit the magnitude of the voltage Vy, to be always less than IyZt for control method 1, or always greater than IyZt. This way the resonance never collapses. If Zt and Iy are known it is possible to know how close to the power limit the system is operating. If the system is operating too close to the limit, the receiver can communicate this information to the transmitter, which can turn up its output, Vx, effectively turning up Vt, so the system can transfer more power. For example, in some embodiments, if a difference between IyZt and Vy is less than a predetermined threshold, the receiver transmits a control message to the transmitter to cause the transmitter to increase Vx. In this way, the transmitter output can be optimized to run at the minimum current needed, minimizing losses, achieving the most efficient operation possible.

To measure Zt it is possible for the receiver to vary the voltage Vy and observe the change in Iy. Specifically, if Vy is varied by a predetermined amount (referred to as 'dither'), in a sampled data system, we have:

$$Vy[n]=Vy[n-1]\pm dither$$

Further, the Thevenin equivalent impedance is then:

$$Zt[n] = \frac{Vy[n] - Vy[n-1]}{Iy[n] - Iy[n-1]}$$

The values in these equations are phasors. Accordingly, the mathematical operations are performed using complex numbers. This method of calculating Zt works if the voltage Vt is constant and the value of Zt is constant. This will be true if the voltage Vx is constant and the transmitter and receiver are not moving relative to one another. In practice, it can be assumed that any relative movement of the transmitter and receiver is very slow compared to the voltage signal Vy. Further, in practice, Vx is controlled, so it does change. However, as long as the control system driving Vx is slow as compared to the voltage signal Vy, and any relative movement of the transmitter and receiver is relatively slow, the measured result of Zt is close enough to the actual value to facilitate optimizing power transfer.

Figure 9:
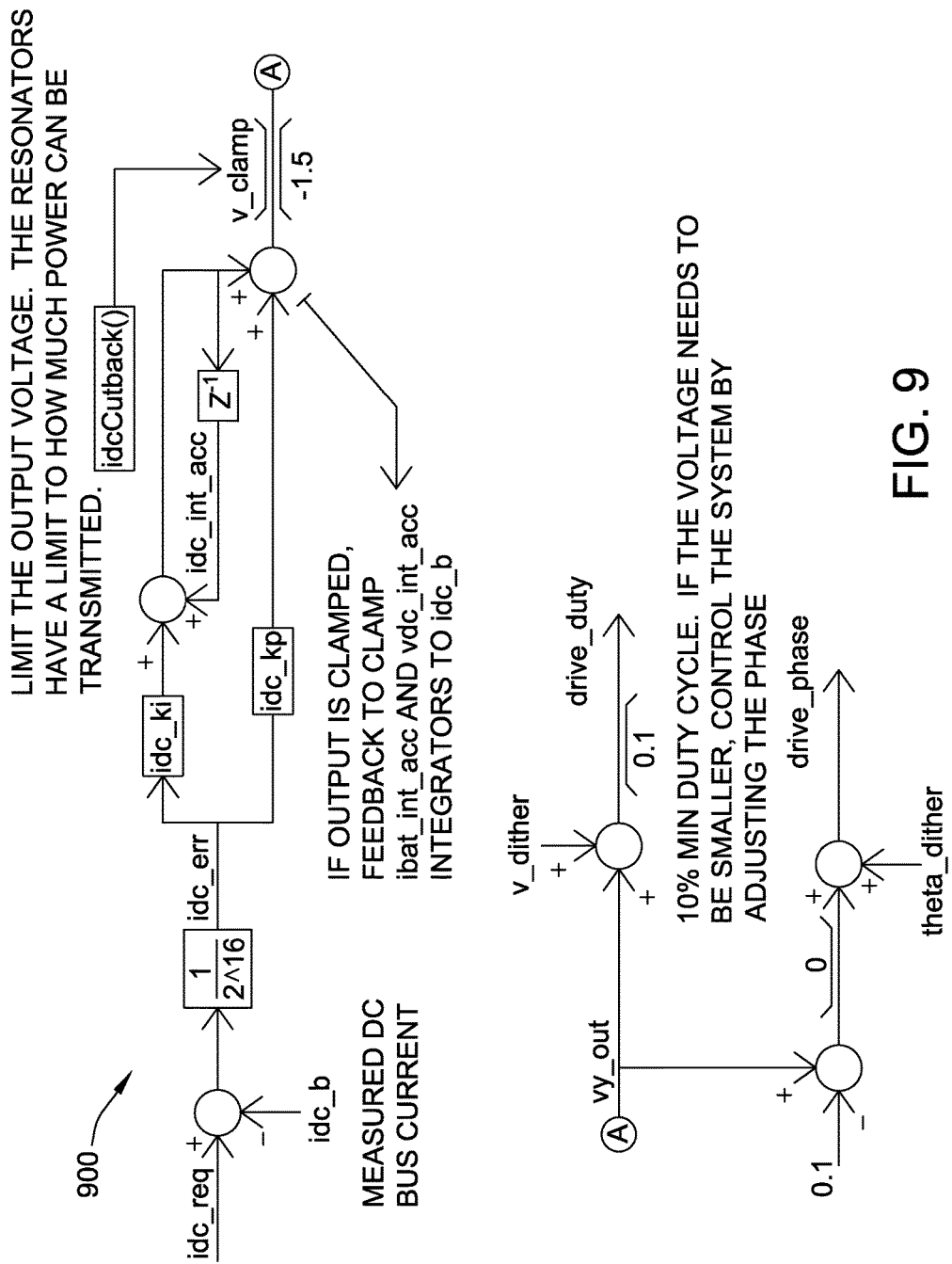
FIG. 9 shows a diagram of a control system for a receiver according to one embodiment of the present disclosure.

FIG. 9 shows a diagram of one embodiment of a control system 900 for a receiver according to one embodiment of the present disclosure. In this embodiment, control system 900 is implemented using the receiver electronics. Control system 900 adjusts the magnitude and phase of the voltage signal Vy in order to achieve a desired current Idcy (shown in FIG. 5). Control system 900 is used when IyZt is larger than Vy, so that increasing Vy results in an increase in power received by the receiver.

In this embodiment, the voltage Vy is driven by a MOSFET bridge 502 (shown in FIG. 5) that connects the Vdcy and Vy circuits. MOSFET bridge 502 is controlled by a pulse width modulated signal from a microcontroller (e.g., as part of the receiver electronics). Specifically, control system 900 controls a duty cycle and phase of the pulse width modulated signal, resulting in Vy. The phase is controlled such that Vy is almost always in phase with Iy. The exception occurs when the desired voltage is very small (at which point the duty cycle is clamped at a minimum value and control system 900 adjusts the phase of the output voltage).

In this embodiment, control system 900 adjusts Vy in order to achieve a described Idcy value. The amount of desired current is based on the demands of the receiver. In this embodiment, control system 900 is implemented using a proportional integrative (PI) controller. Alternatively, control system 900 may be implemented using any suitable controller. The output of the PI controller is limited by v_clamp, as shown in FIG. 9. v_clamp is the maximum allowed voltage and is calculated by a function called IdcCutback. This function observers the resonator impedance (Zt) and calculates IyZt. In this embodiment, the magnitude of IyZt is the maximum voltage possible for Vy, and IyZt is used for v_clamp. This facilitates limiting the power the receiver can pull from the resonant system to prevent the resonance from collapsing.

Figure 10:
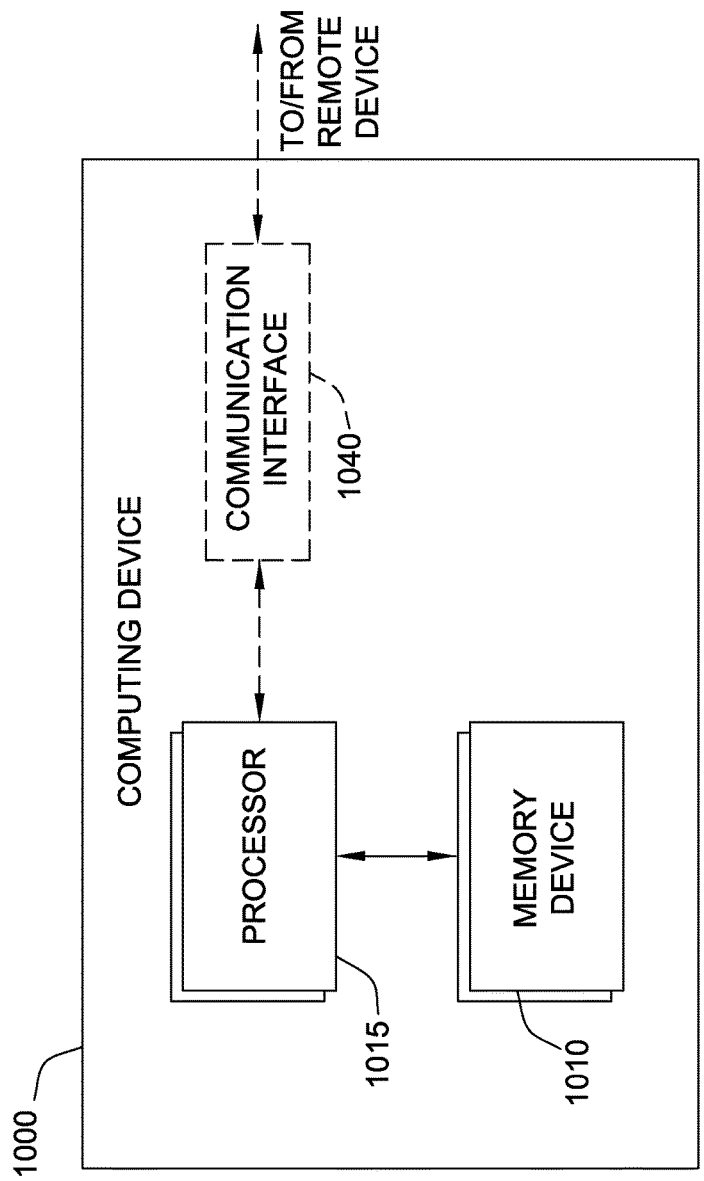
FIG. 10 is a block diagram of one embodiment of a computing device that may be used to implement receiver electronics.

In some embodiments, the receiver electronics are implemented as a computing device. For example, FIG. 10 is a block diagram of one embodiment of a computing device 1000 that may be used to perform the functions of the receiver electronics.

In this embodiment, computing device 1000 includes at least one memory device 1010 and a processor 1015 that is coupled to memory device 1010 for executing instructions. In some embodiments, executable instructions are stored in memory device 1010. In the illustrated embodiment, computing device 1000 performs one or more operations described herein by programming processor 1015. For example, processor 1015 may be programmed by encoding an operation as one or more executable instructions and by providing the executable instructions in memory device 1010.

Processor 1015 may include one or more processing units (e.g., in a multi-core configuration). Further, processor 1015 may be implemented using one or more heterogeneous processor systems in which a main processor is present with secondary processors on a single chip. In another illustrative example, processor 1015 may be a symmetric multi-processor system containing multiple processors of the same type. Further, processor 1015 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 1010 is one or more devices that enable information such as executable instructions and/or other data to be stored and retrieved. Memory device 1010 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. Memory device 1010 may be configured to store, without limitation, application source code, application object code, source code portions of interest, object code portions of interest, configuration data, execution events and/or any other type of data.

Computing device 1000, in the illustrated embodiment, includes a communication interface 1040 coupled to processor 1015. Communication interface 240 communicates with one or more remote devices, such as the transmitter. To communicate with remote devices, communication interface 140 may include, for example, a wired network adapter, a wireless network adapter, a radio-frequency (RF) adapter, and/or a mobile telecommunications adapter.

Figure 11:
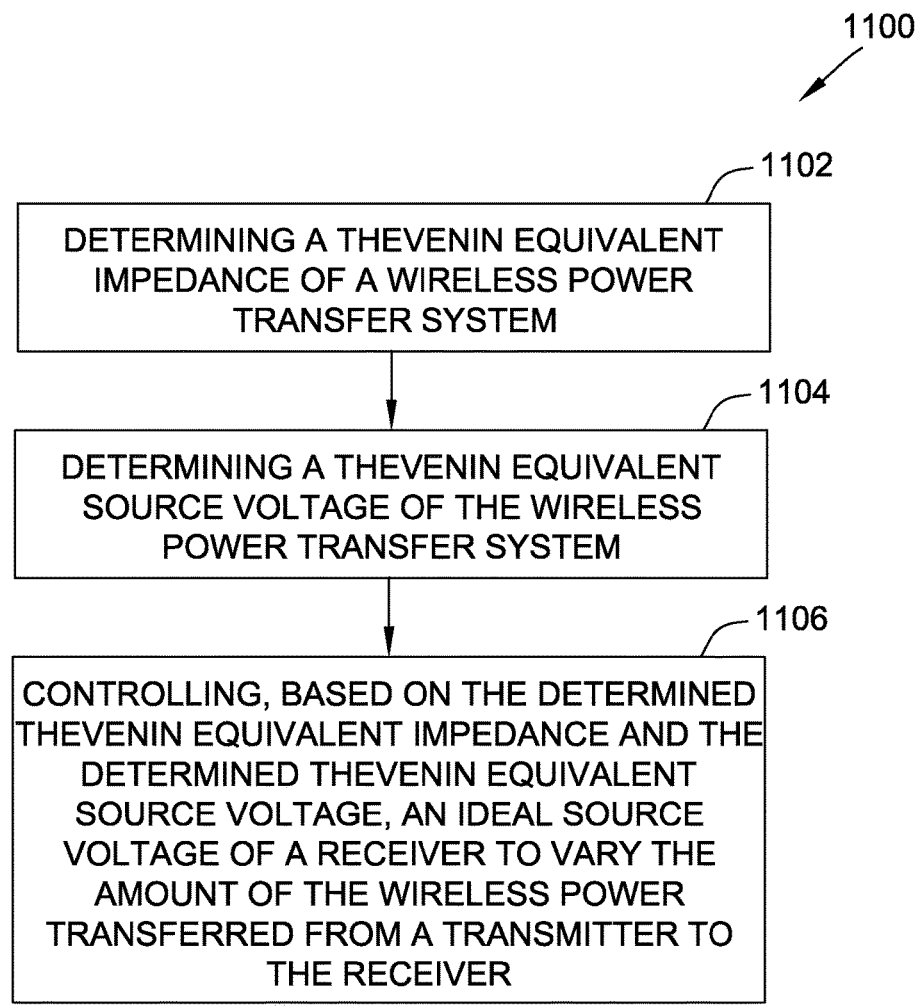
FIG. 11 is a flow chart of one embodiment of a method for controlling operation of a wireless power transfer system.

FIG. 11 is a flow chart of one embodiment of a method 1100 for controlling a wireless power transfer system. Method 1100 may be implemented, for example, using computing device 1000 (shown in FIG. 10). In this embodiment, method 1100 includes determining 1102 a Thevenin equivalent impedance of the wireless power transfer system. Method 1100 further includes determining 1104 a Thevenin equivalent source voltage of the wireless power transfer system. Method 1100 further includes controlling 1106, based on the determined Thevenin equivalent impedance and the determined Thevenin equivalent source voltage, an ideal source voltage of the receiver to vary the amount of the wireless power transferred from the transmitter to the receiver.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims. Although described in some respects as a medical system, one will appreciate from the description herein that the principles can apply equally to other types of systems including, but not limited to, consumer electronics, automotive, phones and personal communication devices, gaming devices, and computers and peripherals.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wireless power transfer system comprising:
   a transmitter driven by a power source and a transmit controller, wherein the transmitter is configured to control delivery of wireless power; and
   a receiver inductively coupled to the transmitter, the receiver configured to receive the wireless power from the transmitter and deliver the received wireless power to a load via a converter circuit, the receiver including receiver electronics configured to:
      vary an ideal source voltage of the receiver at an input of the converter circuit;
      monitor changes in an ideal source current at the input of the converter circuit while varying the ideal source voltage;
      calculate a Thevenin equivalent impedance of the wireless power transfer system based on the monitored changes in the ideal source current at the input of the converter circuit;
      calculate a Thevenin equivalent source voltage of the wireless power transfer system based on the Thevenin equivalent impedance; and
      control the converter circuit, based on the calculated Thevenin equivalent impedance and the calculated Thevenin equivalent source voltage, to control the ideal source voltage to vary an amount of the wireless power transferred from the transmitter to the receiver.

2. The wireless power transfer system of claim 1, wherein the receiver electronics are further configured to:
   determine that the load requires additional power; and
   transmit a control message to the transmitter that causes the transmitter to provide additional wireless power.

3. The wireless power transfer system of claim 1, wherein to control the converter circuit to control the ideal source voltage of the receiver, the receiver electronics are configured to:
   compare the Thevenin equivalent source voltage to the ideal source voltage; and
   control the converter circuit to control the ideal source voltage based on the comparison.

4. The wireless power transfer system of claim 3, wherein to control the converter circuit to control the ideal source voltage based on the comparison, the receiver electronics are configured to control the converter circuit to increase the ideal source voltage when the Thevenin equivalent source voltage is greater than the ideal source voltage.

5. The wireless power transfer system of claim 3, wherein to control the converter circuit to control the ideal source voltage based on the comparison, the receiver electronics are configured to control the converter circuit to decrease the ideal source voltage when the Thevenin equivalent source voltage is less than the ideal source voltage.

6. The wireless power transfer system of claim 1, wherein to control the converter circuit to control the ideal source voltage of the receiver, the receiver electronics are configured to:

calculate a power limit voltage as a product of the Thevenin equivalent impedance and the ideal source current; and control the converter circuit to control the ideal source voltage such that the ideal source voltage is always less than the power limit voltage or always greater than the power limit voltage.

7. The wireless power transfer system of claim 6, wherein the receiver electronics are further configured to:

determine that a difference between the power limit voltage and the ideal source voltage is less than a predetermined value; and transmit a control message to the transmitter that causes the transmitter to increase the Thevenin equivalent source voltage by increasing an output voltage of the transmitter at an output of a transmitter converter circuit.

8. A receiver for use in a wireless power transfer system, the receiver configured to receive wireless power from a transmitter driven by a power source and a transmit controller, and configured to deliver the received wireless power to a load via a converter circuit, the receiver comprising:

a receiving coil; and receiver electronics coupled to the receiving coil, the receiver electronics configured to:

vary an ideal source voltage of the receiver at an input of the converter circuit;

monitor changes in an ideal source current at the input of the converter circuit while varying the ideal source voltage;

calculate a Thevenin equivalent impedance of the wireless power transfer system based on the monitored changes in the ideal source current at the input of the converter circuit;

calculate a Thevenin equivalent source voltage of the wireless power transfer system based on the Thevenin equivalent impedance; and control the converter circuit, based on the calculated Thevenin equivalent impedance and the calculated Thevenin equivalent source voltage, to control the ideal source voltage to vary an amount of the wireless power transferred from the transmitter to the receiver.

9. The receiver of claim 8, wherein the receiver electronics are further configured to:

determine that the load requires additional power; and transmit a control message to the transmitter that causes the transmitter to provide additional wireless power.

10. The receiver of claim 8, wherein to control the converter circuit to control the ideal source voltage of the receiver, the receiver electronics are configured to:

compare the Thevenin equivalent source voltage to the ideal source voltage; and control the converter circuit to control the ideal source voltage based on the comparison.

11. The receiver of claim 10, wherein to control the converter circuit to control the ideal source voltage based on the comparison, the receiver electronics are configured to control the converter circuit to increase the ideal source voltage when the Thevenin equivalent source voltage is greater than the ideal source voltage.

12. The receiver of claim 10, wherein to control the converter circuit to control the ideal source voltage based on the comparison, the receiver electronics are configured to control the converter circuit to decrease the ideal source voltage when the Thevenin equivalent source voltage is less than the ideal source voltage.

13. The receiver of claim 8, wherein to control the ideal source voltage of the receiver, the receiver electronics are configured to:

calculate a power limit voltage as a product of the Thevenin equivalent impedance and the ideal source current; and control the converter circuit to control the ideal source voltage such that the ideal source voltage is always less than the power limit voltage or always greater than the power limit voltage.

14. The receiver of claim 13, wherein the receiver electronics are further configured to:

determine that a difference between the power limit voltage and the ideal source voltage is less than a predetermined value; and transmit a control message to the transmitter that causes the transmitter to increase the Thevenin equivalent source voltage by increasing an output voltage of the transmitter at an output of a transmitter converter circuit.

15. A method for controlling a wireless power transfer system, the wireless power transfer system including a receiver inductively coupled to a transmitter, the receiver configured to receive wireless power from the transmitter and deliver the received wireless power to a load via a converter circuit, the method comprising:

varying an ideal source voltage of the receiver at an input of the converter circuit monitoring changes in an ideal source current at the input of the converter circuit while varying the ideal source voltage;

calculating, using receiver electronics at the receiver, a Thevenin equivalent impedance of the wireless power transfer system based on the monitored changes in the ideal source current at the input of the converter circuit;

calculating, using the receiver electronics, a Thevenin equivalent source voltage of the wireless power transfer system based on the Thevenin equivalent impedance; and controlling the converter circuit, using the receiver electronics, based on the calculated Thevenin equivalent impedance and the calculated Thevenin equivalent source voltage, to control the ideal source voltage to vary an amount of the wireless power transferred from the transmitter to the receiver.

16. The method of claim 15, further comprising:

determining that the load requires additional power; and transmitting a control message to the transmitter that causes the transmitter to provide additional wireless power.

17. The method of claim 15, wherein controlling the converter circuit to control the ideal source voltage of the receiver comprises:

comparing the Thevenin equivalent source voltage to the ideal source voltage; and controlling the converter circuit to control the ideal source voltage based on the comparison.

18. The method of claim 15, wherein controlling the converter circuit to control the ideal source voltage of the receiver comprises:

calculating a power limit voltage as a product of the Thevenin equivalent impedance and the ideal source current; and controlling the converter circuit to control the ideal source voltage such that the ideal source voltage is always less than the power limit voltage or always greater than the power limit voltage.

* * * * *